(12) United States Patent
Jiao et al.

(10) Patent No.: US 12,121,237 B2
(45) Date of Patent: Oct. 22, 2024

(54) SURGICAL STAPLING APPARATUS WITH TISSUE GAP LOCK

(71) Applicant: Covidien LP, Mansfield, MA (US)

(72) Inventors: Yanjun Jiao, Shanghai (CN); Xiliang Zhang, Shanghai (CN); Yuandong Tan, Shanghai (CN)

(73) Assignee: Covidien LP, Mansfield, MA (US)

( * ) Notice: Subject to any disclaimer, the term of this patent is extended or adjusted under 35 U.S.C. 154(b) by 88 days.

(21) Appl. No.: 17/917,749

(22) PCT Filed: Apr. 28, 2020

(86) PCT No.: PCT/CN2020/087425
§ 371 (c)(1),
(2) Date: Oct. 7, 2022

(87) PCT Pub. No.: WO2021/217404
PCT Pub. Date: Nov. 4, 2021

(65) Prior Publication Data
US 2023/0157694 A1 May 25, 2023

(51) Int. Cl.
*A61B 17/064* (2006.01)
*A61B 17/115* (2006.01)

(52) U.S. Cl.
CPC ................. *A61B 17/1155* (2013.01)

(58) Field of Classification Search
CPC ................. A61B 17/07292; A61B 17/1155
See application file for complete search history.

(56) References Cited

U.S. PATENT DOCUMENTS

| | | | |
|---|---|---|---|
| 5,915,616 | A | 6/1999 | Viola et al. |
| 5,964,394 | A | 10/1999 | Robertson |
| 6,945,444 | B2 | 9/2005 | Gresham et al. |
| 7,128,253 | B2 | 10/2006 | Mastri et al. |
| 7,334,717 | B2 | 2/2008 | Rethy et al. |
| 7,819,896 | B2 | 10/2010 | Racenet |
| 8,109,426 | B2 | 2/2012 | Milliman et al. |
| 8,157,152 | B2 | 4/2012 | Holsten et al. |
| 8,256,656 | B2 | 9/2012 | Milliman et al. |
| 8,272,552 | B2 | 9/2012 | Holsten et al. |
| 9,307,994 | B2 | 4/2016 | Gresham et al. |
| 9,414,839 | B2 | 8/2016 | Penna |
| 9,492,168 | B2 | 11/2016 | Milliman |
| 9,504,470 | B2 | 11/2016 | Milliman |

(Continued)

FOREIGN PATENT DOCUMENTS

CN 1989912 A 7/2007
CN 104939885 A * 9/2015 ........... A61B 7/1155

(Continued)

OTHER PUBLICATIONS

Extended European Search Report issued in corresponding European Application No. 20933611.4 dated Jan. 2, 2024, 11 pages.

(Continued)

*Primary Examiner* — Eyamindae C Jallow

(57) ABSTRACT

A circular stapling apparatus including a stationary handle, a trigger pivotably coupled to the stationary handle, a trigger lock selectively engageable with the trigger, and a firing link coupled to the trigger. The firing link has a catch thereon. The trigger lock has a latch assembly that is selectively engageable with the catch.

20 Claims, 7 Drawing Sheets

(56) References Cited

U.S. PATENT DOCUMENTS

| | | | |
|---|---|---|---|
| 2007/0257082 A1* | 11/2007 | Milliman | A61B 17/072 227/175.1 |
| 2008/0190991 A1* | 8/2008 | Milliman | A61B 17/072 227/175.1 |
| 2009/0173767 A1* | 7/2009 | Milliman | A61B 17/115 227/179.1 |
| 2010/0108741 A1* | 5/2010 | Hessler | A61B 17/068 227/179.1 |
| 2010/0301098 A1* | 12/2010 | Kostrzewski | A61B 17/115 227/176.1 |
| 2012/0116416 A1 | 5/2012 | Neff et al. | |
| 2013/0175315 A1* | 7/2013 | Milliman | A61B 17/1155 227/175.1 |
| 2013/0175318 A1* | 7/2013 | Felder | A61B 17/115 227/175.1 |
| 2013/0175320 A1 | 7/2013 | Mandakolathur Vasudevan et al. | |
| 2013/0334279 A1* | 12/2013 | Prior | A61B 17/064 227/175.1 |
| 2014/0158745 A1 | 6/2014 | Milliman | |
| 2020/0029969 A1 | 1/2020 | Wang et al. | |

FOREIGN PATENT DOCUMENTS

| | | |
|---|---|---|
| CN | 104224260 B | 8/2016 |
| CN | 108403176 A | 8/2018 |
| EP | 2298181 A1 | 3/2011 |
| EP | 2790592 B1 | 10/2015 |
| WO | 2014139440 A1 | 9/2014 |
| WO | 2016025132 A1 | 2/2016 |

OTHER PUBLICATIONS

International Search Report for Application No. PCT/CN2020/087425 dated Jan. 28, 2021.
Written Opinion for Application No. PCT/CN2020/087425 dated Jan. 28, 2021.

* cited by examiner

SURGICAL STAPLING APPARATUS WITH TISSUE GAP LOCK

TECHNICAL FIELD

This disclosure relates to surgical stapling apparatus and, more particularly, to structures and methods for locking tissue gap.

BACKGROUND

Fasteners have traditionally been used to replace suturing when joining various body structures such as, for example, the bowel or bronchus. Surgical stapling apparatus employed to apply these fasteners are generally designed to simultaneously cut and seal tissue to reduce the time and risks involved with anastomosis procedures.

Circular surgical stapling apparatus are employed by surgeons to apply one or more surgical fasteners, e.g., staples or two-part fasteners, to body tissue for the purpose of joining segments of body tissue together and/or for the creation of anastomoses. Circular surgical stapling apparatus generally include an annular fastener cartridge assembly that supports a plurality of annular rows of fasteners, an annular anvil assembly operatively associated with the fastener cartridge assembly which provides a surface against which the fasteners are formed upon a firing of the circular stapling apparatus, and an annular blade for cutting tissue.

SUMMARY

According to one aspect, a surgical stapling apparatus includes a handle assembly, an elongated central body portion extending distally from the handle assembly to a distal end portion, and an end effector supported on the distal end portion of the elongated central body portion. The handle assembly includes a stationary handle and a trigger. The handle assembly further includes a trigger lock that is pivotably coupled to the stationary handle and selectively engageable with the trigger to prevent movement of the trigger relative to the stationary handle. The trigger is coupled to a firing link having a catch thereon. The trigger lock has a latch assembly. The end effector has an anvil assembly and a cartridge assembly. The anvil and cartridge assemblies are positionable between an unclamped position and a clamped position to selectively grasp tissue therebetween. The trigger lock and the latch assembly are selectively engageable to lock the anvil and cartridge assemblies in the clamped position.

In aspects, the firing link may be pivotably coupled to the trigger on a first end portion thereof. The catch may be disposed on a second end portion of the firing link. The latch assembly may include a support wall and a latch extending from the support wall. The catch may define a capture recess that is configured to receive the latch therein.

In various aspects, a drive screw assembly may be operatively coupled to the anvil assembly to enable the anvil assembly to move relative to the cartridge assembly. A screw stop may be supported on the drive screw assembly. The screw stop may be positioned to engage a pivot member supported by the firing link. The screw stop may include an engagement tooth depending therefrom. The engagement tooth may be positioned to engage a shaft of the pivot member in a screw stop channel defined in the firing link. The pivot member may prevent the screw stop from advancing distally to lock the anvil and cartridge assemblies in the clamped position when the trigger lock is disengaged from the trigger. An approximation knob may be rotatable to axially move the screw stop relative to the stationary handle.

According to another aspect, a circular stapling apparatus includes a stationary handle, a trigger pivotably coupled to the stationary handle, a trigger lock, and a firing link coupled to the trigger. The trigger lock is selectively engageable with the trigger and has a latch assembly. The firing link has a catch thereon that is selectively engageable with the latch assembly.

In aspects, the firing link may be pivotably coupled to the trigger.

In various aspects, the catch may be in the form of a hook.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, serve to explain the principles of this disclosure, wherein.

DETAILED DESCRIPTION

Figure 1:
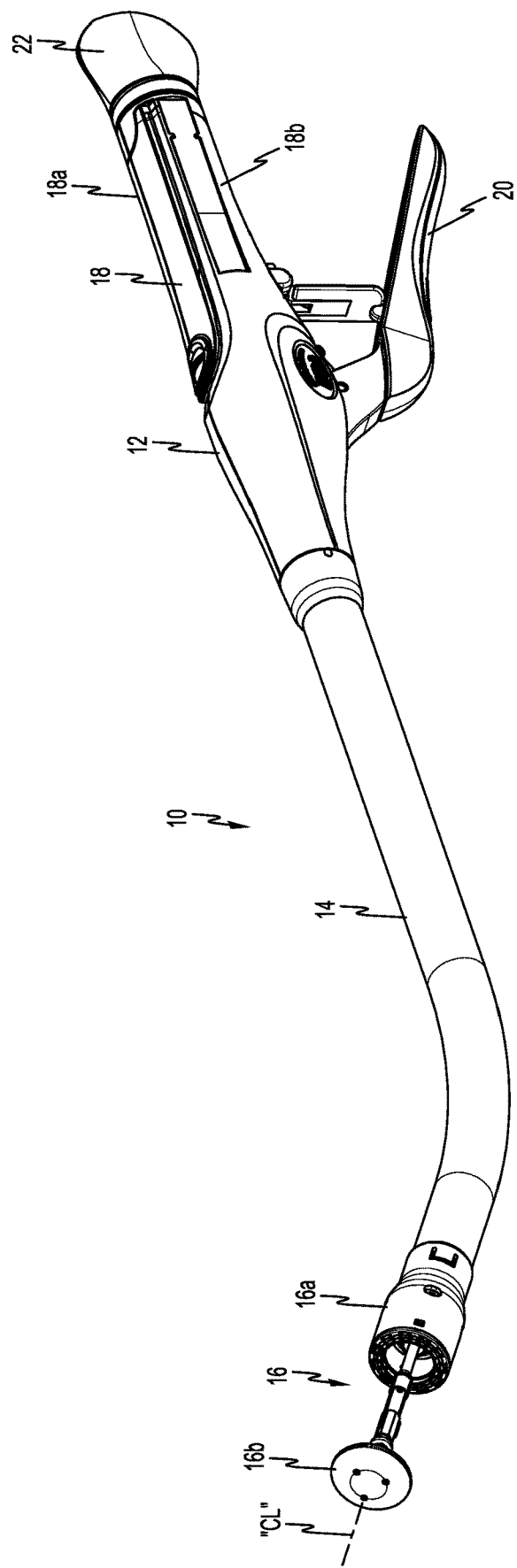
FIG. 1 is a perspective view of a surgical stapling apparatus in accordance with the principles of this disclosure with an end effector thereof shown in an unclamped position.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring this disclosure in unnecessary detail.

Further, although the surgical instrument described herein is provided in connection with a manual surgical stapling apparatus for brevity, the disclosed surgical instrument can include any powered, manual, or robotically-controlled surgical instruments such as a clip applier, stitching device, energy-based device (e.g., a bipolar or monopolar forceps) or the like, and/or other surgical stapling apparatus such as a laparoscopic stapler, a transverse stapler, or an open stapler. For a detailed description of the structure and function of exemplary surgical stapling apparatus, one or more components of which may be included, or modified for use with the disclosed aspects, reference may be made to U.S. Patent Application Publication No. 2020/0029969 or U.S. Pat. Nos. 9,504,470; 9,414,839; 8,272,552, 8,256,656; 8,157,152; 8,109,426; 7,819,896; 7,334,717; 7,128,253; 5,964,394; and 5,915,616, the entire contents of each of which is incorporated herein by reference.

Briefly, a trigger lock of a circular stapling apparatus engages a trigger of the circular stapling apparatus to obstruct the trigger and prevent the circular stapling apparatus from inadvertently firing. To fire the circular stapling apparatus, the trigger lock can be moved to an open position to enable the trigger of the circular stapling apparatus to actuate for firing the circular stapling apparatus. Before firing, however, it is desirable to lock a tissue gap defined between anvil and cartridge assemblies to improve staple formation. Unfortunately, internal space within the circular stapling apparatus is limited. The disclosed circular stapling apparatus provides a solution for locking the tissue gap without adding internal components. More specifically, this disclosure details a solution in the handle that enables the circular stapling apparatus to lock the tissue gap after the trigger lock is opened, but before the circular stapling apparatus is fired. Setting the tissue gap to a predetermined or fixed size when the trigger lock is opened improves staple formation. This solution also provides a reduction in the span of the trigger relative to the stationary handle resulting in better ergonomics and usability.

Turning now to FIGS. 1-8, a surgical stapling apparatus, generally referred to as 10, is illustrated. Surgical stapling device 10 defines a centerline "CL" and includes a proximal handle assembly 12, an elongated central body portion 14 that extends distally from the proximal handle assembly 12, and an end effector or a distal tool assembly 16 supported on a distal end portion of the elongated central body portion 14. The distal tool assembly 16 includes a cartridge or shell assembly 16a and an anvil assembly 16b that cooperate to fasten tissue together. In particular, the shell assembly 16a and the anvil assembly 16b are positionable between an unclamped or unapproximated position (see FIG. 1) and a clamped or approximated position (see FIG. 5) to selectively secure tissue therebetween for selectively stapling and/or cutting the clamped tissue.

The handle assembly 12 of the surgical stapling device 10 includes a stationary handle 18, a firing trigger 20, and a rotatable approximation knob 22. The stationary handle 18 of the handle assembly 12 is formed from handle sections 18a and 18b, which, when secured together, define a housing for the internal components of the handle assembly 12. The handle assembly 12 further includes a pivotally mounted trigger lock 24 fastened to the handle sections 18a and 18b on a first end portion 24a of the trigger lock 24; a second end portion 24b of trigger lock 24 is free. The first end portion 24a of the trigger lock 24 includes a latch assembly 25 that is selectively engageable with a firing link 44 of the surgical stapling device 10. Latch assembly 25 includes a support wall 25a that extends outwardly from the trigger lock 24 and a latch 25b that extends laterally from an upper portion of the support wall 25a. The second end portion 24b (e.g., a lower free end portion) of the trigger lock 24 is manually positioned in engagement with a trigger lock mount 20x on the firing trigger 20 to obstruct movement of the firing trigger 20 and prevent inadvertent firing of the stapling device 10. The stationary handle 18 includes a bulbous indicator 19 that is supported on an upper surface of the stationary handle 18 to provide an indication to the clinician when the shell assembly 16a and the anvil assembly 16b of the distal tool assembly 16 of the stapling device 10 are approximated and in a fire-ready or clamped position.

Figure 2:
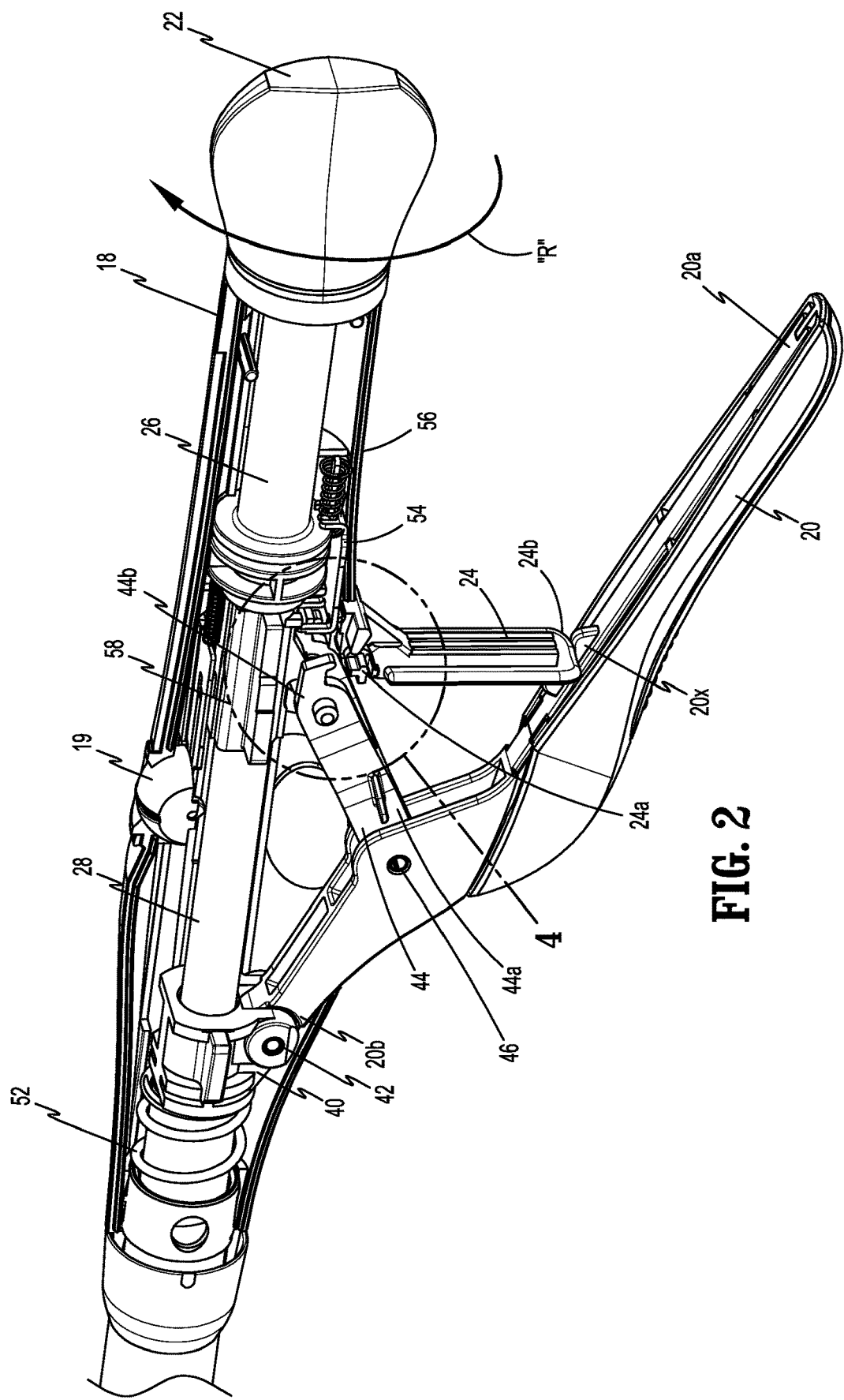
FIG. 2 is an enlarged, perspective view of a proximal end portion of the surgical stapling apparatus of FIG. 1 with portions of the proximal end portion removed for clarity and a trigger lock of the proximal end portion shown in a first position.

With reference to FIG. 2, a distal end portion of the approximation knob 22 of the handle assembly 12 is rotatably fixed to a proximal end portion of a rotatable sleeve 26 such that rotation of the knob 22, as indicated by arrows "R," causes concurrent rotation of the sleeve 26. The rotatable sleeve 26 extends distally from the approximation knob 22 and receives a drive screw assembly 28 that is operatively coupled to anvil assembly 16b to enable anvil assembly 16b to move relative to shell assembly 16a in response to rotation of approximation knob 22.

Figure 3:
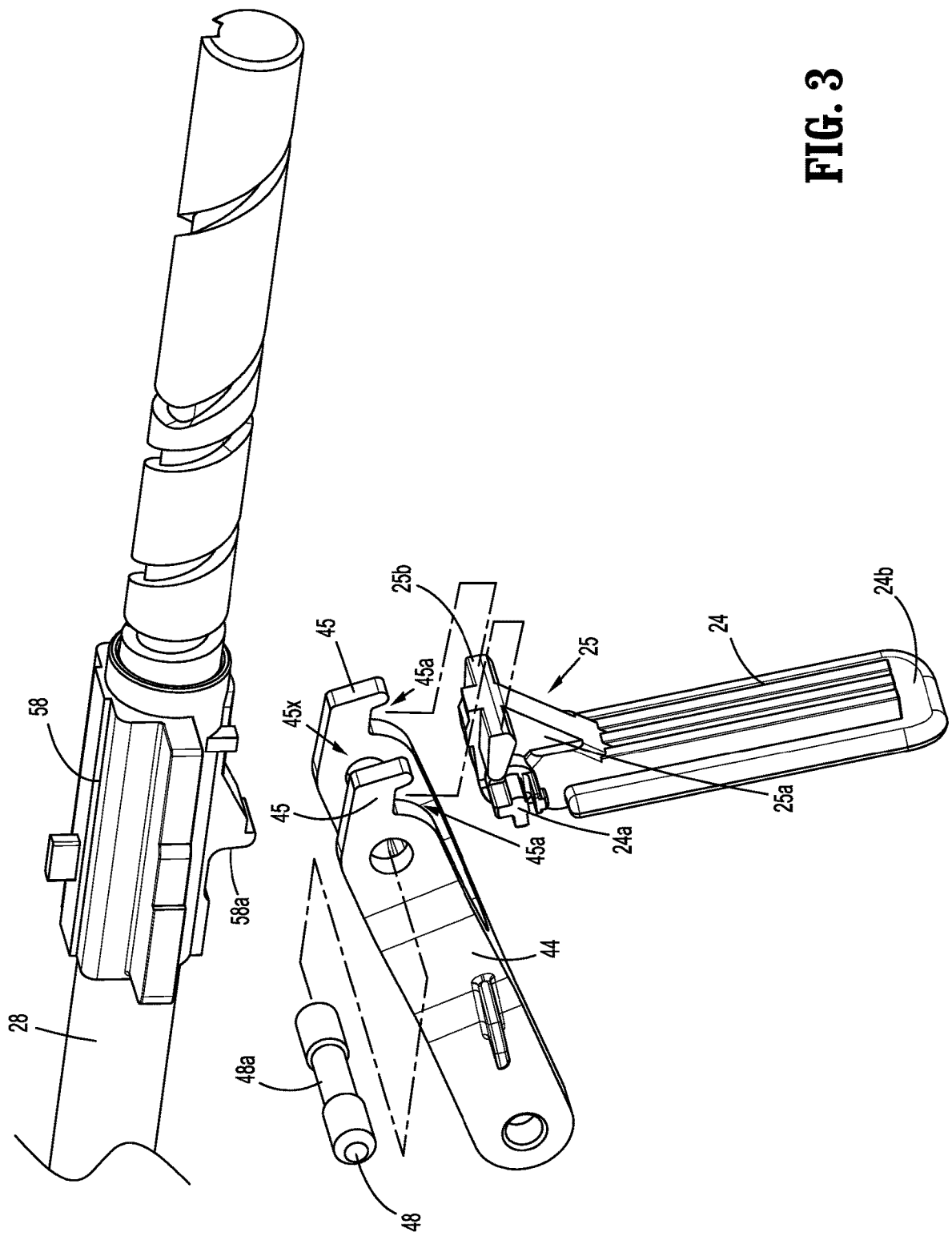
FIG. 3 is a perspective view, with parts separated, of various components of the proximal end portion of the surgical stapling apparatus of FIG. 2.
Figure 4:
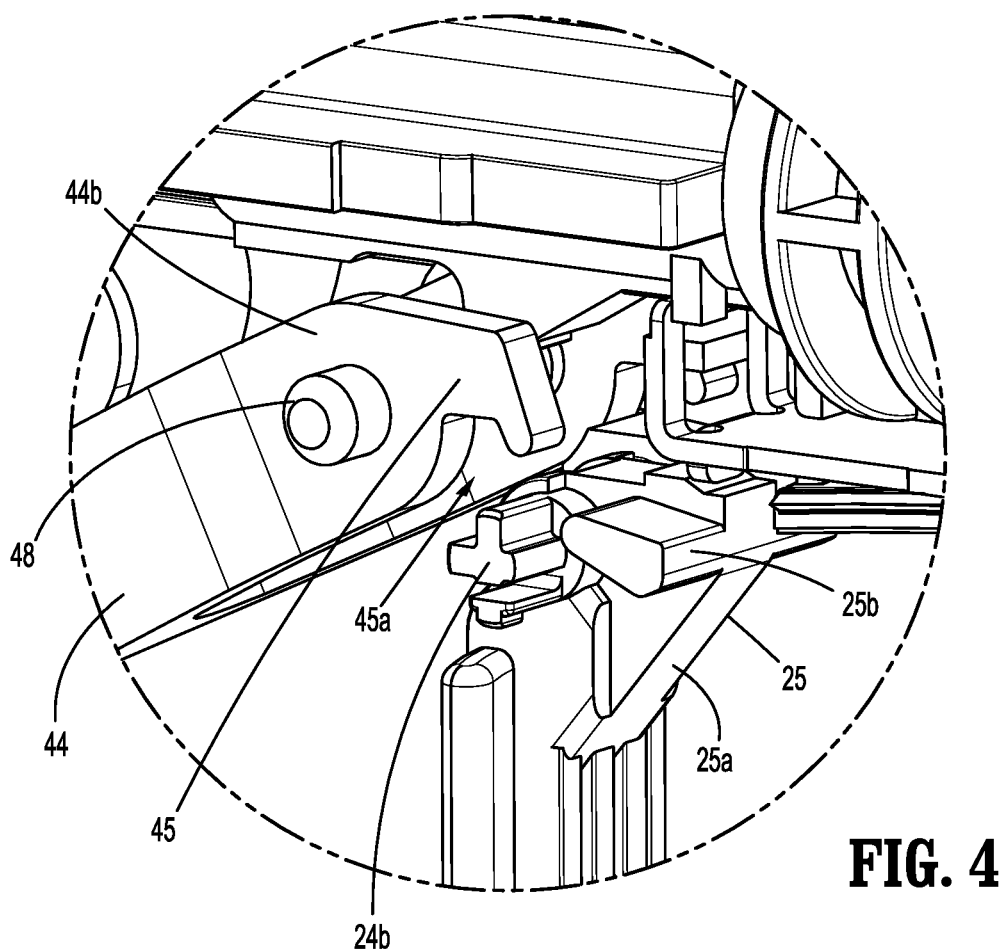
FIG. 4 is an enlarged view of the indicated area of detail shown in FIG. 2.

With continued reference to FIG. 2, the firing trigger 20 of the handle assembly 12 has a proximal portion 20a and a distal portion 20b. The distal portion 20b of the firing trigger 20 is pivotally connected to an elongated pusher link 40 by a pivot member 42 to facilitate pivotal movement of the firing trigger 20 relative to the stationary handle 18 of the handle assembly 12. The firing trigger 20 of the handle assembly 12 is pivotally connected to a first end portion 44a of a firing link 44 by a pivot member 46. The firing link 44 includes a second end portion 44b that is pivotally secured to the stationary handle 18 by a pivot member 48. As seen in FIGS. 3 and 4, the second end portion 44b of firing link 44 further includes catches 45, which may be in the form of hooks, that are laterally spaced apart from one another to define a screw stop channel 45x therebetween. Catches 45 define capture recesses 45a that are concave and positioned to receive and selectively capture a latch assembly 25 of trigger lock 24 therein.

The elongated pusher link 40 is slidably supported within the central body portion 14 of the surgical stapling device 10 about the drive screw assembly 28 along the central body portion 14 between a retracted, nonfired position and an advanced, fired position. The elongated pusher link 40 supports a spring 52 (FIG. 3) about an outer surface thereof to bias the elongated pusher link 40 proximally toward the retracted, non-fired position.

Referring again to FIG. 3, the handle assembly 12 of the surgical stapling device 10 slidably supports a lockout member 54 (FIG. 2) within the handle assembly 12 between retracted and advanced positions. The lockout member 54 is biased by a coil spring 56 toward the advanced position to maintain the trigger lock 24 in a locked position to prevent actuation of the firing trigger 20 of the handle assembly 12. The drive screw assembly 28 includes a screw stop 58 that is axially fixed thereon, and that is movable from an advanced position located adjacent to the elongated pusher link 40 (corresponding to an unclamped position of anvil assembly 16b) to a retracted position located adjacent to the rotatable sleeve 26 (corresponding to a clamped position of anvil assembly 16b) (see FIG. 2) to control the degree of movement of the anvil assembly 16b of the distal tool assembly 16 in relation to the shell assembly 16a of the distal tool assembly 16 such as disclosed in U.S. Pat. Nos. 6,945,444, 9,307,994, and 9,492,168, the contents of each of which are incorporated by reference herein in their entirety.

Screw stop 58 includes an engagement tooth 58a (FIG. 3) depending therefrom that is selectively engageable with a shaft 48a of pivot member 48.

Figure 5:
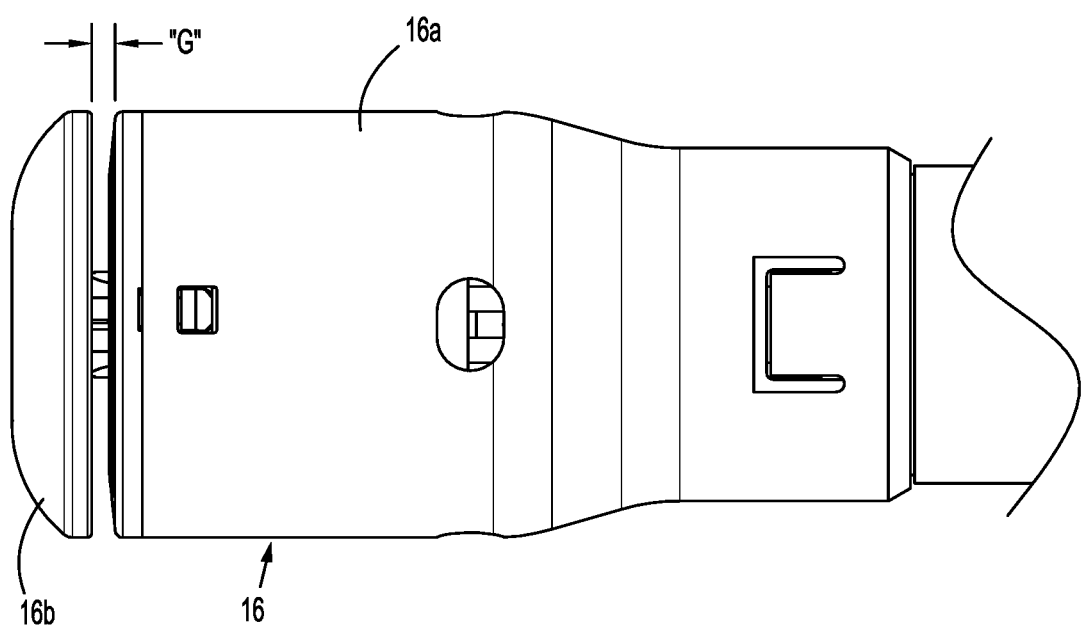
FIG. 5 is an enlarged, side view of the end effector of FIG. 1 shown in a clamped position.
Figure 6:
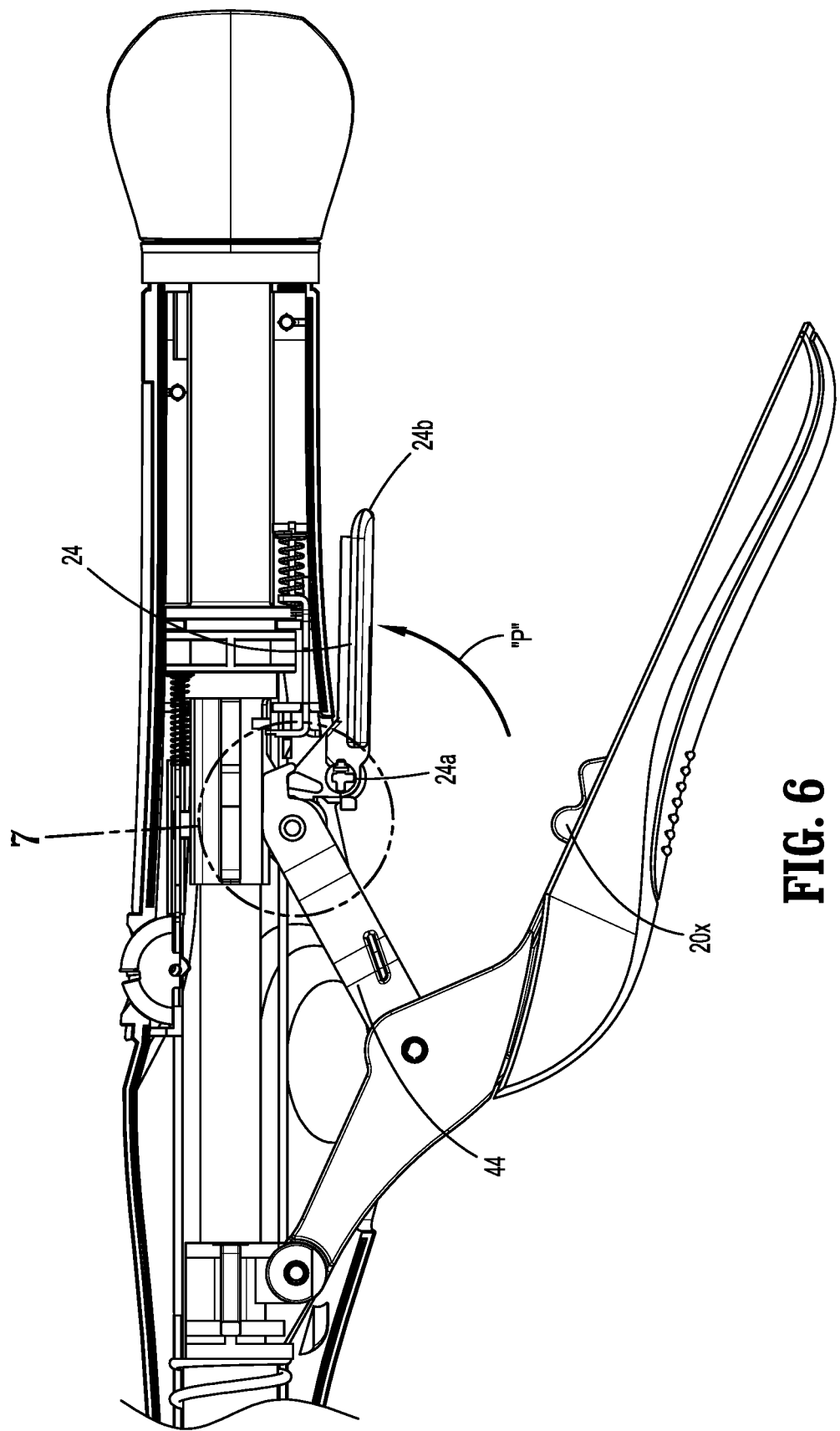
FIG. 6 is an enlarged, side view of the proximal end portion of FIG. 2 with the trigger lock shown in a second position.
Figure 7:
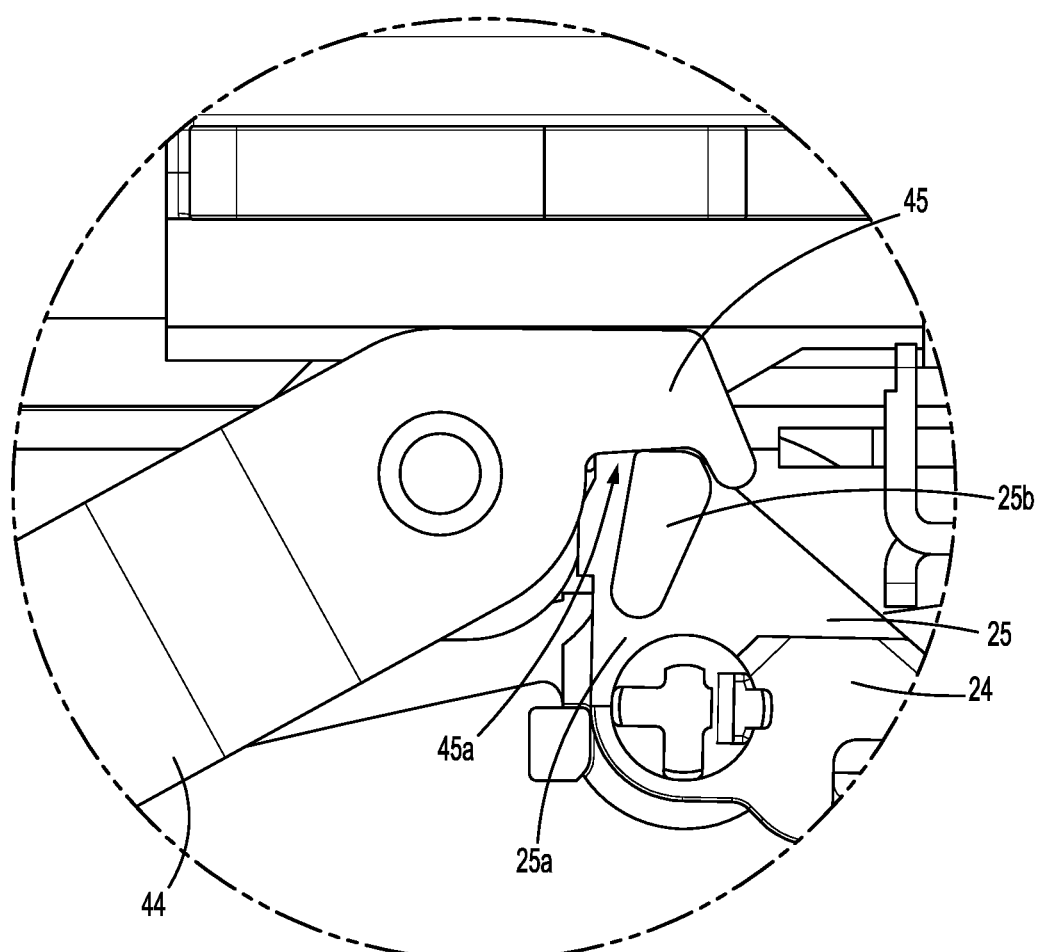
FIG. 7 is an enlarged view of the indicated area of detail shown in FIG. 6.
Figure 8:
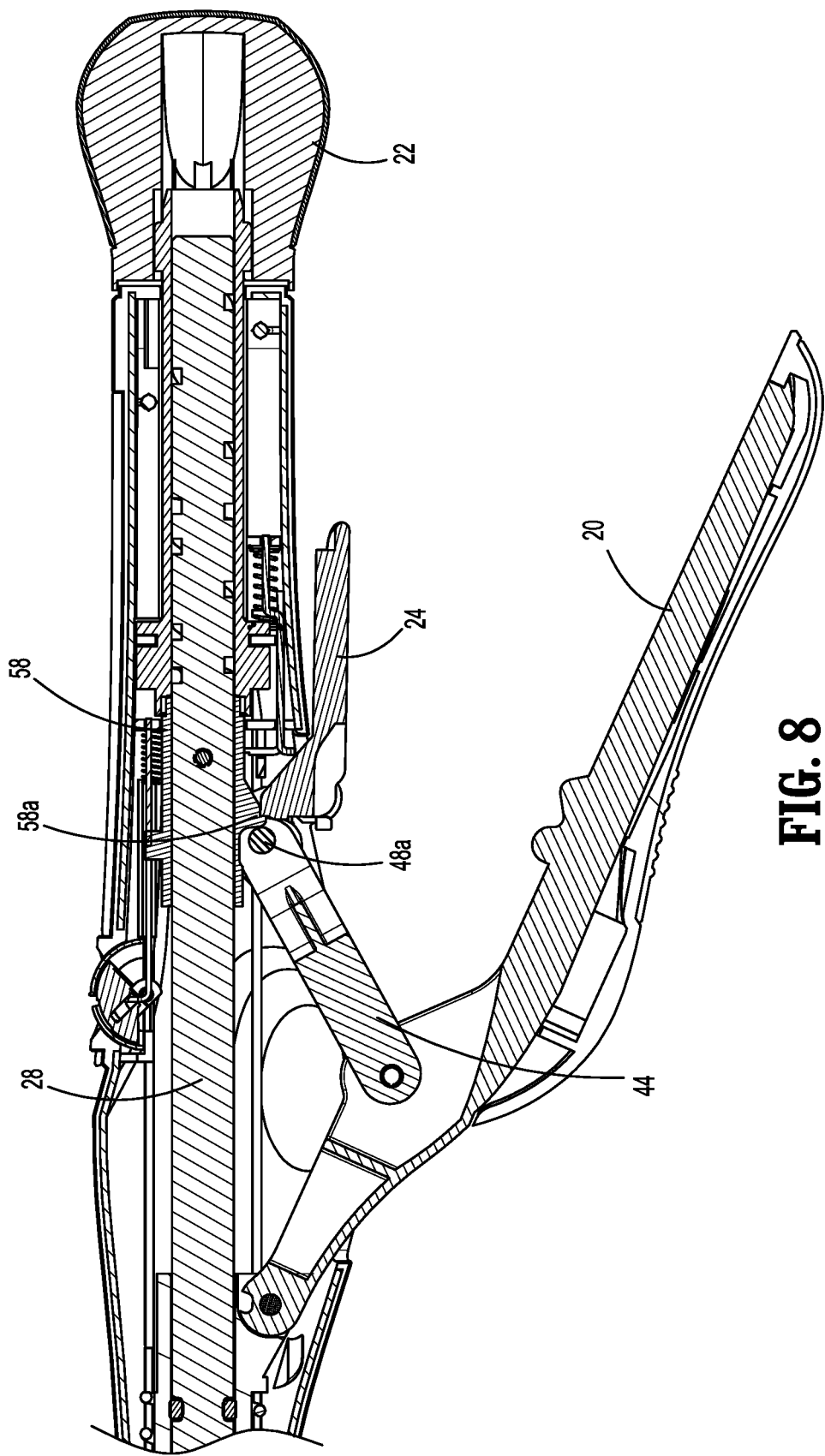
FIG. 8 is a side view, in longitudinal cross-section, of the proximal end portion shown in FIG. 6.

With continued reference to FIGS. 1-8, in order to unlock the firing trigger 20 from the trigger lock mount 20x, the drive screw assembly 28 and the screw stop 58 are drawn proximally by rotation of the approximation knob 22. During approximation of the shell assembly 16a and the anvil assembly 16b, the screw stop 58 moves proximally so that the screw stop 58 contacts the lockout member 54 and drives the lockout member 54 proximally against the bias of (e.g., tension in) the coil spring 56. The approximation knob 22 can be rotated until the anvil assembly 16b are disposed in the clamped position (FIG. 5). Proximal movement of the lockout member 54 separates the lockout member 54 from contact with the trigger lock 24 and enables the second end portion 24b of the trigger lock 24 to pivot away from both the trigger lock mount 20x and the firing trigger 20, as indicated by arrow "P" (FIG. 6). As the second end portion 24b of the trigger lock 24 pivots toward the stationary handle 18, the catch recesses 45a of catches 45 of firing link 44 capture latch 25b of latch assembly 25 of trigger lock 24 as latch 25b cams therein as seen in FIG. 7. With latch assembly 25 secured to catches 45, engagement tooth 58a of screw stop 58 is distally obstructed by shaft 48a of pivot member 48 of firing link 44, preventing screw stop 58 from moving distally and thereby preventing anvil assembly 16b from unapproximating or unclamping to maintain tissue gap "G" (FIG. 5). Indeed, the combination of the latch assembly 25 and the catches 45 provide self-locking structure and function. For instance, when the surgical stapling device 10 is ready for firing, but the clinician mistakenly rotates approximation knob 22 in a direction that attempts to open or unapproximate (e.g., counterclockwise) the cartridge assembly 16a and the anvil assembly 16b, the capture latch 25b will self-lock with the catch recesses 45a and the trigger lock 245 will engage with the stationary handle 18 to prevent the cartridge assembly 16a and the anvil assembly 16b from unapproximating. And, if the capture latch 25b is not already disposed within the catch recesses 45a, the rotation of the approximation knob 22 will cause the capture latch 25b to fall into the catch recesses 45a Notably, with trigger lock 24 pivoted away from the firing trigger 20, the span of the firing trigger 20 relative to stationary handle 18 (e.g., firing trigger 20 at smaller angle relative to stationary handle 18) reduces so that the firing trigger 20 can be actuated with greater ergonomics/usability and with improved staple formation on account of the fixed or substantially fixed tissue gap "G."

Once firing is complete, trigger lock 24 is pivoted back into engagement with trigger lock mount 20x of firing trigger 20 so engagement tooth 58a of screw stop 58 is clear of pivot member 48 and approximation knob 22 can be rotated to unapproximate or unclamp the anvil assembly 16b and the shell assembly 16a.

Further, the various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

As can be appreciated, securement of any of the components of the disclosed apparatus can be effectuated using known securement techniques such welding, crimping, gluing, fastening, etc.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling apparatus, comprising:
a handle assembly including a stationary handle and a trigger, the handle assembly further including a trigger lock that is pivotably coupled to the stationary handle and selectively engageable with the trigger to prevent movement of the trigger relative to the stationary handle, the trigger coupled to a firing link having a catch thereon, the trigger lock having a latch assembly;
an elongated central body portion extending distally from the handle assembly to a distal end portion;
an end effector supported on the distal end portion of the elongated central body portion, the end effector having an anvil assembly and a cartridge assembly, the anvil and cartridge assemblies positionable between an unclamped position and a clamped position to selectively grasp tissue therebetween, the trigger lock and the latch assembly selectively engageable to lock the anvil and cartridge assemblies in the clamped position; and a drive screw assembly having an engagement tooth engageable with a pivot member supported by the firing link to maintain the anvil and cartridge assemblies in the clamped position.

2. The surgical stapling apparatus of claim 1, wherein the firing link is pivotably coupled to the trigger on a first end portion thereof.

3. The surgical stapling apparatus of claim 2, wherein the catch is disposed on a second end portion of the firing link.

4. The surgical stapling apparatus of claim 3, wherein the latch assembly includes a support wall and a latch extending from the support wall.

5. The surgical stapling apparatus of claim 4, wherein the catch defines a capture recess that is configured to receive the latch therein.

6. The surgical stapling apparatus of claim 1, wherein the drive screw assembly is operatively coupled to the anvil assembly to enable the anvil assembly to move relative to the cartridge assembly.

7. The surgical stapling apparatus of claim 6, wherein a screw stop is supported on the drive screw assembly, the engagement tooth extending from the screw stop.

8. The surgical stapling apparatus of claim 7, wherein the engagement tooth is positioned to engage a shaft of the pivot member in a screw stop channel defined by the firing link.

9. The surgical stapling apparatus of claim 8, wherein the pivot member prevents the screw stop from advancing distally to lock the anvil and cartridge assemblies in the clamped position when the trigger lock is disengaged from the trigger.

10. The surgical stapling apparatus of claim 7, further comprising an approximation knob that is rotatable to axially move the screw stop relative to the stationary handle.

11. A circular stapling apparatus, comprising:
a stationary handle;
a trigger pivotably coupled to the stationary handle;
a trigger lock selectively engageable with the trigger and having a latch assembly;
a firing link coupled to the trigger and having a catch thereon that is selectively engageable with the latch assembly;
a pivot member supported by the firing link; and
a drive screw assembly having an engagement tooth engageable with the pivot member to maintain an end effector of the circular stapling apparatus in a clamped position.

12. The circular stapling apparatus of claim 11, wherein the firing link is pivotably coupled to the trigger.

13. The circular stapling apparatus of claim 11, wherein the catch is in the form of a hook.

14. The circular stapling apparatus of claim 11, wherein the latch assembly includes a support wall and a latch extending from the support wall.

15. The circular stapling apparatus of claim 14, wherein the catch defines a capture recess that is configured to receive the latch therein.

16. The circular stapling apparatus of claim 11, wherein the drive screw assembly is operatively coupled to an anvil assembly to enable the anvil assembly to move relative to a cartridge assembly.

17. The circular stapling apparatus of claim 16, wherein a screw stop is supported on the drive screw assembly, the engagement tooth extending from the screw stop.

18. The circular stapling apparatus of claim 17, wherein the engagement tooth is positioned to engage a shaft of the pivot member in a screw stop channel defined by the firing link.

19. The circular stapling apparatus of claim 18, wherein the pivot member prevents the screw stop from advancing distally to lock the anvil and cartridge assemblies in the clamped position when the trigger lock is disengaged from the trigger.

20. The circular stapling apparatus of claim 17, further comprising an approximation knob that is rotatable to axially move the screw stop relative to the stationary handle.

* * * * *